United States Patent
Lim et al.

(10) Patent No.: US 11,150,555 B2
(45) Date of Patent: Oct. 19, 2021

(54) PHOTOACID GENERATOR AND CHEMICALLY AMPLIFIED POSITIVE-TYPE PHOTORESIST COMPOSITION FOR THICK FILM COMPRISING THE SAME

(71) Applicant: LG CHEM, LTD., Seoul (KR)

(72) Inventors: Min Young Lim, Daejeon (KR); Tae Seob Lee, Daejeon (KR); Ji Hye Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 279 days.

(21) Appl. No.: 16/337,280

(22) PCT Filed: Apr. 3, 2018

(86) PCT No.: PCT/KR2018/003923
§ 371 (c)(1),
(2) Date: Mar. 27, 2019

(87) PCT Pub. No.: WO2019/050120
PCT Pub. Date: Mar. 14, 2019

(65) Prior Publication Data
US 2020/0033724 A1  Jan. 30, 2020

(30) Foreign Application Priority Data

Sep. 11, 2017 (KR) ........................ 10-2017-0116135

(51) Int. Cl.
*G03F 7/004* (2006.01)
*C07D 221/14* (2006.01)
*G03F 7/039* (2006.01)

(52) U.S. Cl.
CPC ......... *G03F 7/0045* (2013.01); *C07D 221/14* (2013.01); *G03F 7/039* (2013.01)

(58) Field of Classification Search
CPC ...... G03F 7/039; G03F 7/0392; G03F 7/0045; G03F 7/0046; G03F 7/038; G03F 7/0382; C07D 221/14
See application file for complete search history.

(56) References Cited

U.S. PATENT DOCUMENTS 9,477,150 B2   10/2016 Zhang et al.
2006/0182751 A1  8/2006 Gazzard et al.
2007/0298006 A1  12/2007 Tomalia et al.
2012/0289697 A1  11/2012 Murai et al.
2015/0241783 A1*  8/2015 Carcasi ................ G03F 7/2004
                                                    430/324
2015/0299132 A1* 10/2015 Hirahara ............. C07D 409/04
                                                    546/98
2016/0266487 A1   9/2016 Zhang et al.
2016/0368879 A1  12/2016 Ikeda et al.
2017/0003587 A1   1/2017 Zhang et al.

FOREIGN PATENT DOCUMENTS

| CN | 101284827 A | 10/2008 |
| CN | 104797560 A | 7/2015 |
| EP | 2998297 A1 | 3/2016 |
| JP | 2013-127517 A | 6/2013 |
| JP | 2014-094926 A | 5/2014 |
| JP | 2017-126044 A | 7/2017 |
| KR | 10-2012-0114353 A | 10/2012 |
| KR | 10-2015-0087846 A | 7/2015 |
| KR | 10-2016-0030210 A | 3/2016 |
| KR | 10-2016-0048144 A | 5/2016 |
| WO | 2016-148809 A1 | 9/2016 |
| WO | 2017-034814 A1 | 3/2017 |

OTHER PUBLICATIONS

Liu, Y. et al., "Synthesis and properties of starburst amorphous molecules: 1,3,5-Tris(1,8-naphthalimide-4-yl) benzenes", Synthetic Metals, 2010, 160, p. 2055-2060.
Qin, A. et al., "Hyperbranched Polytriazoles: Click Polymerization, Regioisomeric Structure, Light Emission, and Fluorescent Patterning", Macromolecules, 2008, 41, p. 3808-3822.
International Search Report and Written Opinion issued for PCT application No. PCT/KR2018/003923 dated Jul. 30, 2018, 10 pages.

\* cited by examiner

*Primary Examiner* — John A McPherson
*Assistant Examiner* — Nicholas E Brown
(74) *Attorney, Agent, or Firm* — Rothwell, Figg, Ernst and Manbeck, P.C.

(57) ABSTRACT

A non-ionic photoacid generator and a chemically amplified positive-type photoresist composition for a thick film including the non-ionic photoacid generator. The non-ionic photoacid generator may not only exhibit high solubility in a solvent of the photoresist composition, but may also exhibit chemical and thermal stability and high sensitivity. In particular, the non-ionic photoacid generator is decomposed by light to generate an acid, and at the same time, can exhibit a corrosion preventing effect on a metal substrate.

14 Claims, No Drawings

PHOTOACID GENERATOR AND CHEMICALLY AMPLIFIED POSITIVE-TYPE PHOTORESIST COMPOSITION FOR THICK FILM COMPRISING THE SAME

CROSS-REFERENCE TO RELATED APPLICATION

This application is a 35 U.S.C. § 371 National Phase Entry Application from PCT/KR2018/003923, filed on Apr. 3, 2018, and designating the United States, which claims the benefits of Korean Patent Application No. 10-2017-0116135 filed on Sep. 11, 2017 with the Korean Intellectual Property Office, the disclosure of which are incorporated herein by reference in their entirety.

Technical Field

The present disclosure relates to a photoacid generator and a chemically amplified positive-type photoresist composition for a thick film including the same.

Background of Art

Photofabrication is the mainstay of microfabrication technology, and packaging technology is constantly changing to a process for manufacturing high-density packages.

In particular, as the number of input/output terminals of semiconductors increases, the use of a flip-chip has expanded and fan-out wafer level packaging (FOWLP) technology has been introduced. In addition, a TSV (Through-Silicon Via) process, which enables direct chip-to-chip connection to minimize signal delay, has expanded, and the demand for bumps has increased. Thus, it is considered important to develop a technology for a bump photoresist which forms the bump.

The bump photoresist requires (i) excellent sensitivity and resolution in a thick film up to 10 to 100 micrometers, (ii) good pattern performance such as straightness, residue characteristics, footing, and notching characteristics to form metal bumps by a plating process, and (iii) excellent resistance to a plating solution.

Therefore, a chemically amplified photoresist is used to increase sensitivity and resolution in a thick film. Generally, the chemically amplified photoresist composition includes (a) a resin dissociated by an acid to increase solubility in an alkali developer, (b) a photosensitive acid generator (a photoacid generator), (c) an acid diffusion controller, (d) a corrosion inhibitor, and (e) a dissolution inhibitor.

The photoacid generator is a substance which is decomposed by light to generate an acid, and is divided into an ionic compound and a non-ionic compound. The acid generated from the photoacid generator drops protecting groups of the resin in the resist so that a pattern can be formed.

However, the naphthalimide-type photoacid generator, which has been conventionally used, has a poor solubility in a solvent, so that a large amount of the photoacid generator is required to increase the sensitivity. But the addition amount thereof has an upper limit, and there is a problem that scum is left in an exposure part after development when an excess amount is added.

DETAILED DESCRIPTION OF THE INVENTION

Technical Problem

The present disclosure is to provide a non-ionic photoacid generator exhibiting excellent solubility in a solvent, and high sensitivity and corrosion inhibition.

In addition, the present disclosure is to provide a chemically amplified positive-type photoresist composition for a thick film including the non-ionic photoacid generator.

Technical Solution

According to the present disclosure, a non-ionic photoacid generator including at least one functional group represented by the following Chemical Formula 1 is provided.

[Chemical Formula 1]

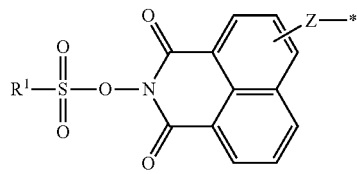

In Chemical Formula 1, $R^1$ is a C1 to C10 aliphatic hydrocarbon group substituted or unsubstituted with at least one of a halogen atom, an alkylthio group, and an alicyclic hydrocarbon group; a C1 to C10 perfluoroalkyl group; a C6 to C20 aryl group substituted or unsubstituted with at least one of a halogen atom, an alkylthio group, an alkyl group, and an acyl group; or a C7 to C20 arylalkyl group substituted or unsubstituted with a halogen atom and an alkylthio group, and Z is a divalent group derived from triazole.

In addition, according to the present disclosure, a chemically amplified positive-type photoresist composition for a thick film including the non-ionic photoacid generator is provided.

Hereinafter, the non-ionic photoacid generator and the chemically amplified positive-type photoresist composition for a thick film including the same according to the exemplary embodiments of the present disclosure will be described in more detail.

In this specification, the terms are used merely to refer to specific embodiments, and are not intended to restrict the present disclosure unless it is explicitly expressed.

Singular expressions of the present disclosure may include plural expressions unless it is differently expressed contextually.

The terms "include", "comprise", and the like of the present disclosure are used to specify certain features, regions, integers, steps, operations, elements, and/or components, and these do not exclude the existence or the addition of other certain features, regions, integers, steps, operations, elements, and/or components.

In the chemical formulae of the present disclosure, the symbol

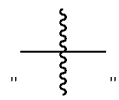

indicates a part where the group is connected to the non-ionic photoacid generator.

In the chemical formulae of the present disclosure, the symbol "*" indicates a part where the group is connected to another group.

I. The Non-Ionic Photoacid Generator

According to an embodiment of the present disclosure, a non-ionic photoacid generator including at least one functional group represented by the following Chemical Formula 1 is provided.

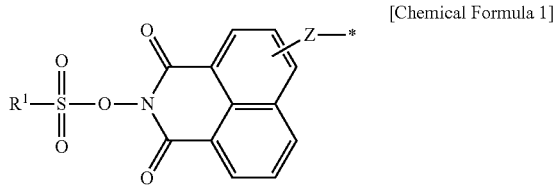

[Chemical Formula 1]

In Chemical Formula 1, $R^1$ is a C1 to C10 aliphatic hydrocarbon group substituted or unsubstituted with at least one of a halogen atom, an alkylthio group, and an alicyclic hydrocarbon group; a C1 to C10 perfluoroalkyl group; a C6 to C20 aryl group substituted or unsubstituted with at least one of a halogen atom, an alkylthio group, an alkyl group, and an acyl group; or a C7 to C20 arylalkyl group substituted or unsubstituted with a halogen atom and an alkylthio group, and Z is a divalent group derived from triazole.

As a result of studies by the present inventors, it was confirmed that the compound including at least one functional group represented by the above Chemical Formula 1 not only exhibits high solubility in a solvent of a photoresist composition, but also exhibits chemical and thermal stability and high sensitivity.

In particular, the compound having a functional group represented by the above Chemical Formula 1 acts as a photoacid generator which is decomposed by light to generate an acid ($R^1SO_3H$), and at the same time, acts as a corrosion inhibitor which can prevent corrosion on metal substrates by the action of the divalent group (—Z—) derived from triazole contained in the decomposed product, as shown in Scheme 1 below.

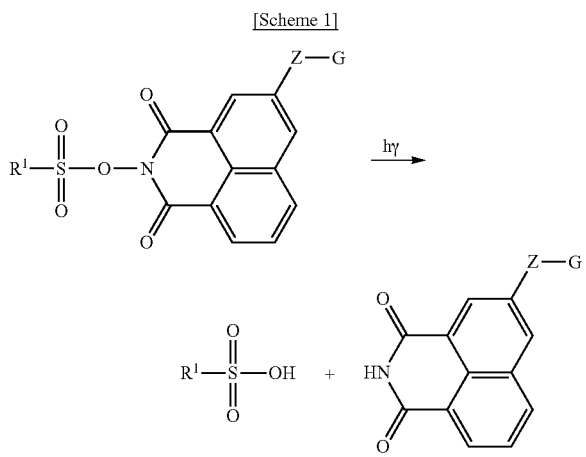

[Scheme 1]

In Scheme 1, $R^1$ and Z are as defined in this specification, and G is any terminal group or central group.

As described above, the compound having the functional group represented by Chemical Formula 1 can be added to the chemically amplified photoresist composition for a thick film as a non-ionic photoacid generator with a corrosion inhibiting effect.

The non-ionic photoacid generator according to an embodiment of the present disclosure is characterized in that it includes at least one functional group represented by the above Chemical Formula 1.

In Chemical Formula 1, $R^1$ is a C1 to C10 aliphatic hydrocarbon group unsubstituted or substituted with at least one of a halogen atom, an alkylthio group, and an alicyclic hydrocarbon group; a C1 to C10 perfluoroalkyl group; a C6 to C20 aryl group unsubstituted or substituted with at least one of a halogen atom, an alkylthio group, an alkyl group, and an acyl group; or a C7 to C20 arylalkyl group unsubstituted or substituted with a halogen atom and an alkylthio group.

For example, $R^1$ may be methyl, ethyl, propyl, isopropyl, butyl, sec-butyl, tert-butyl, isobutyl, amyl, isoamyl, tert-amyl, hexyl, 2-hexyl, 3-hexyl, heptyl, 2-heptyl, 3-heptyl, isoheptyl, tert-heptyl, octyl, isooctyl, tert-octyl, 2-ethylhexyl, nonyl, isononyl, decyl, dodecyl, tridecyl, tetradecyl, pentadecyl, hexadecyl, heptadecyl, octadecyl, trifluoromethyl, pentafluoroethyl, heptafluoropropyl, nonafluorobutyl, tridecylfluorohexyl, heptafluorooctyl, 2,2,2-trifluoroethyl, 1,1-difluoroethyl, 1,1-difluoropropyl, 1,1,2,2-tetrafluoropropyl, 3,3,3-trifluoropropyl, 2,2,3,3,3-pentafluoropropyl, 1,1,2,2-tetrafluorotetradecyl, phenyl, naphthyl, 2-methylphenyl, 3-methylphenyl, 4-methylphenyl, 4-vinylphenyl, 3-isopropylphenyl, 4-isopropylphenyl, 4-butyl phenyl, 4-isobutyl phenyl, 4-tert-butylphenyl, 4-hexyl phenyl, 4-cyclohexyl phenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, 2,5-di-tert-butylphenyl, 2,6-di-tert-butylphenyl, 2,4-di-tert-pentylphenyl, 2,5-di-tert-amylphenyl, 2,5-di-tert-octylphenyl, cyclohexylphenyl, biphenyl, 2,4,5-trimethylphenyl, 2,4,6-trimethylphenyl, 2,4,6-triisopropylphenyl, pentafluorophenyl, chlorophenyl, dichlorophenyl, trichlorophenyl, 2,4-bis(trifluoromethyl)phenyl, bromoethylphenyl, 4-methylthiophenyl, 4-butylthiophenyl, 4-octylthiophenyl, 4-dodecylthiophenyl, 1,2,5,6-tetrafluoro-4-methylthiophenyl, 1,2,5,6-tetrafluoro-4-butylthiophenyl, 1,2,5,6-tetrafluoro-4-dodecylthiophenyl, benzyl, phenethyl, 2-phenylpropan-2-yl, diphenylmethyl, triphenylmethyl, styryl, cinnamyl, pentafluorophenylmethyl, phenyldifluoromethyl, 2-phenyl-tetrafluoroethyl, 2-(pentafluorophenyl)ethyl, p-methylthiobenzyl, 2,3,5,6-tetrafluoro-4-methylthiophenylethyl, acetylphenyl, acetylnaphthyl, benzoylphenyl, 1-anthraquinolyl, 2-anthraquinolyl, or the like.

In Chemical Formula 1, Z is a divalent group derived from triazole.

Preferably, Z may be a group represented by the following Chemical Formula 2a or 2b.

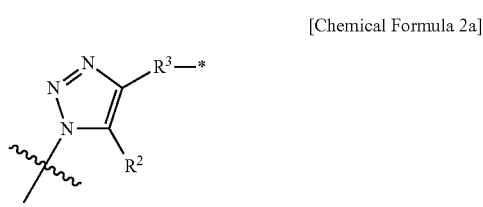

[Chemical Formula 2a]

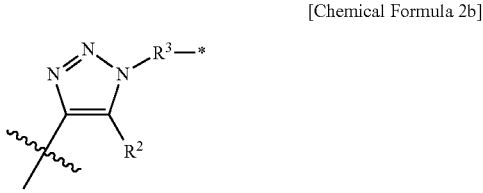

[Chemical Formula 2b]

In Chemical Formulae 2a and 2b,

R² is hydrogen, a C3 to C10 alkyl group, or a C1 to C10 hydroxyalkyl group,

R³ is a chemical bond, a C1 to C10 alkylene group, or a group represented by the following Chemical Formula 3, and R², which is a C3 to C10 alkyl group, and R³, which is a C1 to C10 alkylene group, may be connected to each other to form a C4 to C20 aliphatic ring.

[Chemical Formula 3]

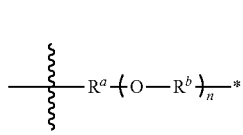

In Chemical Formula 3, $R^a$ is a chemical bond or a C1 to C10 alkylene group, $R^b$ is a C1 to C10 alkylene group, n is an integer of 1 to 10, and when n is 2 or more, each $R^b$, which is repeated two or more times, may be the same or different from each other.

Preferably, R² of the Chemical Formulae 2a and 2b may be hydrogen or a C3 to C10 alkyl group.

When R³ is "a chemical bond" in the above Chemical Formulae 2a and 2b, it means that R³ is a chemical bond which simply links the groups on both sides.

The non-ionic photoacid generator may include at least one functional group represented by Chemical Formula 1. For example, the non-ionic photoacid generator may include one, two, three, or four functional groups represented by the Chemical Formula 1.

The non-ionic photoacid generator may have various forms depending on the chemical structure of the group to which the functional group represented by Chemical Formula 1 is connected.

According to the embodiment of the present disclosure, the non-ionic photoacid generator may be a compound represented by the following Chemical Formula 4a or 4b.

[Chemical Formula 4a]

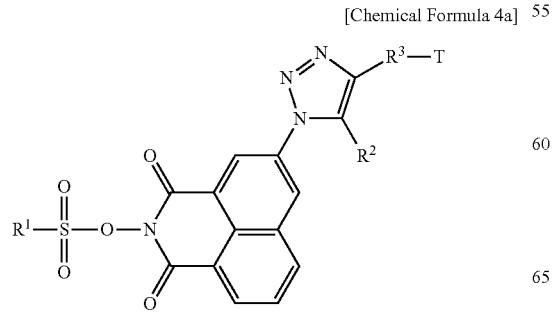

[Chemical Formula 4b]

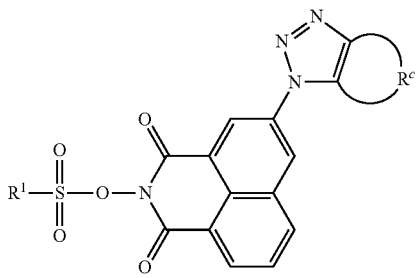

In Chemical Formulae 4a and 4b,

R¹, R², and R³ are as defined above in Chemical Formulae 1, 2a, 2b, and 3,

T is —H, —(C=O)OH, —O—(C=O)OH, —(C=O)NH₂, —NH—(C=O)H, —OCH₃, —SH, —NH₂, —NO₂, —CF₃, or —SF₃, and $R^c$ is a C4 to C20 aliphatic ring.

The compound represented by the following Chemical Formula 4a or 4b is an example of the compound including one functional group represented by Chemical Formula 1, and the present disclosure is not intended to be limited thereto.

In addition, according to the embodiment of the present disclosure, the non-ionic photoacid generator may be a compound represented by the following Chemical Formula 5a or 5b.

[Chemical Formula 5a]

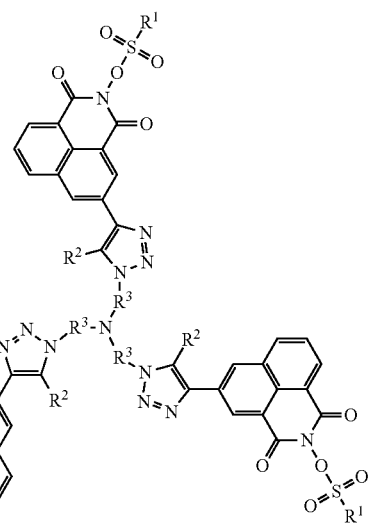

[Chemical Formula 5b]

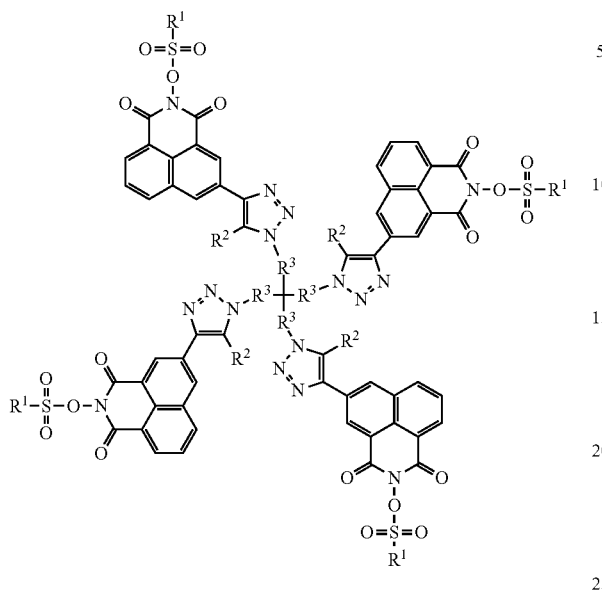

[Scheme 2]

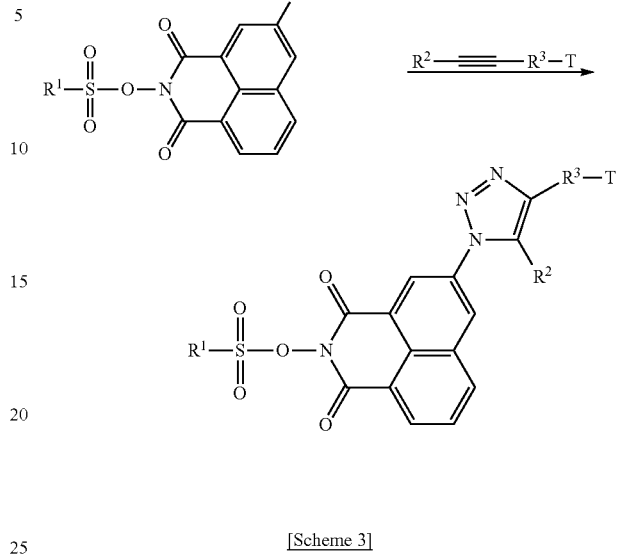

In Chemical Formulae 5a and 5b, $R^1$, $R^2$, and $R^3$ are as defined above in Chemical Formulae 1, 2a, 2b, and 3.

The compound represented by the above Chemical Formula 5a or 5b is an example of the compound including four functional groups which are represented by Chemical Formula 1 and bonded to a central polyfunctional group, and the present disclosure is not intended to be limited thereto.

Meanwhile, the non-ionic photoacid generator according to the embodiment of the present disclosure may be synthesized by a chemical reaction of an azide compound and an alkyne compound (a click reaction).

For example, the non-ionic photoacid generator may be synthesized by a mechanism such as Scheme 2 to 4.

[Scheme 3]

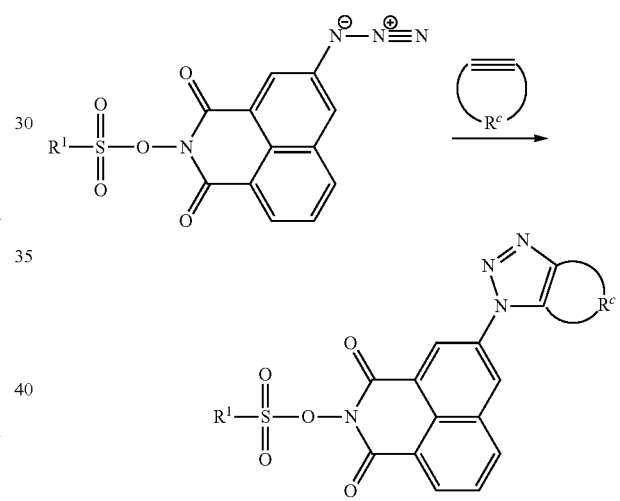

[Scheme 4]

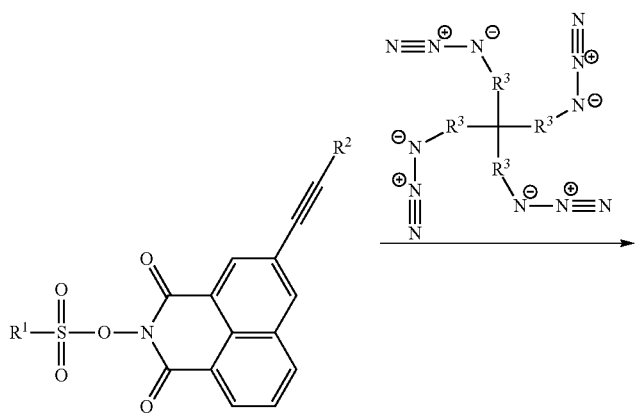

-continued

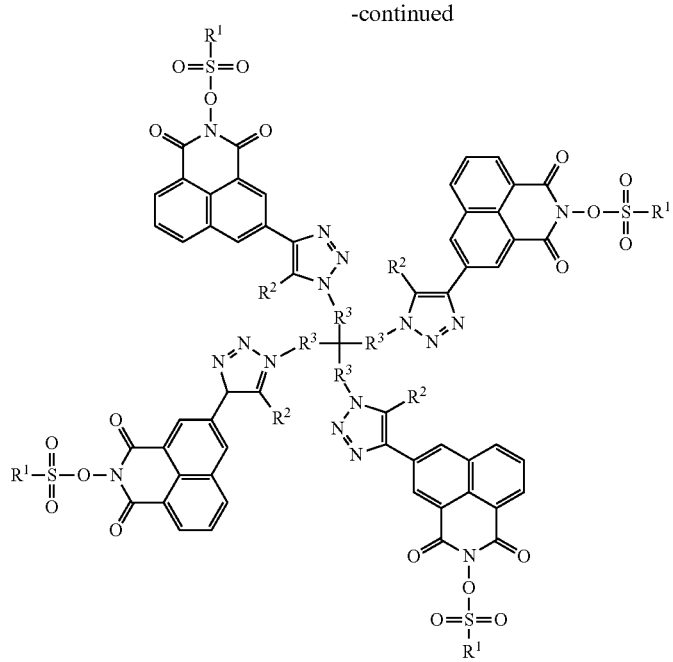

In Scheme 2 to 4, $R^1$, $R^2$, $R^3$, and T are as defined in this specification.

II. The Photoresist Composition

According to another embodiment of the present disclosure, a chemically amplified positive-type photoresist composition for a thick film including the non-ionic photoacid generator including at least one functional group represented by the following Chemical Formula 1 is provided.

[Chemical Formula 1]

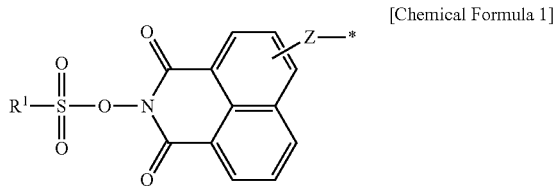

In Chemical Formula 1, $R^1$ is a C1 to C10 aliphatic hydrocarbon group substituted or unsubstituted with at least one of a halogen atom, an alkylthio group, and an alicyclic hydrocarbon group; a C1 to C10 perfluoroalkyl group; a C6 to C20 aryl group substituted or unsubstituted with at least one of a halogen atom, an alkylthio group, an alkyl group, and an acyl group; or a C7 to C20 arylalkyl group substituted or unsubstituted with a halogen atom and an alkylthio group, and Z is a divalent group derived from triazole.

As described above, the non-ionic photoacid generator acts as a photoacid generator which is decomposed by light to generate an acid ($R^1SO_3H$), and at the same time, acts as a corrosion inhibitor which can prevent corrosion on metal substrates by the action of the divalent group (—Z—) derived from triazole contained in the decomposed product.

The chemically amplified positive-type photoresist composition for a thick film according to the present disclosure includes the photoacid generator, thereby exhibiting high sensitivity and not requiring the addition of an additional corrosion inhibitor.

According to an embodiment of the present disclosure, the chemically amplified positive-type photoresist composition for a thick film may further include, in addition to the above-mentioned non-ionic photoacid generator, a resin dissociated by an acid to increase solubility in an alkali developer (hereinafter, an alkali developable resin), a photoinitiator, and an organic solvent.

The alkali developable resin is not particularly limited as long as it is a polymer resin having an acid group protected by a protecting group. The acid group may be, for example, a carboxyl group, a phenolic hydroxyl group, or the like. The alkali developable resin may be a polymer resin that is well known in the art, and may be, for example, a novolac resin, a hydroxystyrene resin, an acrylic resin, or the like.

For example, in order to form a stable pattern, it is preferable that the alkali developable resin contains 30 to 60 wt % of a repeating unit having a functional group that is dissociated by an acid in the molecule.

Further, the alkali developable resin preferably contains 10 to 50 wt % of a repeating unit having a hydrophilic moiety for the purpose of wettability with a plating solution or a developer, adhesion to a substrate, and prevention of cracks.

In addition, in order to prevent cracks or swelling in the photoresist pattern during plating, the alkali developable resin preferably contains 10 to 50 wt % of a hydrophobic bulky repeating unit capable of imparting plating resistance.

Also, sensitivity and speed of development can be controlled by applying monomers having an acidic group or a hydroxyl group to the formation of the alkali developable resin in an amount of 5 to 20 wt %. As the monomers, a compound protected by an acid-deprotected group can be applied.

In addition, it is possible to add monomers capable of controlling heat and chemical resistance in the formation of the alkali developable resin.

The alkali developable resin may have a weight average molecular weight of 10,000 to 300,000 g/mol, 10,000 to 250,000 g/mol, or 12,000 to 200,000 g/mol, which may be advantageous for forming a stable pattern.

As the photoinitiator, a compound that is well known in the art may be used without any particular limitation. For example, the photoinitiator may be benzophenone, an aromatic alpha-hydroxy ketone, a benzyl ketal, an aromatic alpha-amino ketone, a phenylglyoxylic acid ester, a monoacylphosphine oxide, a bis-acylphosphine oxide, a tris-acylphosphine oxide, an oxime ester derived from an aromatic ketone, an oxime ester of a carbazole type, and the like.

The photoinitiator may be included in an amount of 0.1 to 5 parts by weight based on 100 parts by weight of the alkali developable resin, which may be advantageous for manifesting an appropriate photoinitiating effect.

The organic solvent is included to uniformly dissolve various components, to mix them, and to control the viscosity of the photoresist composition. The organic solvent may be applied without limitation as long as it is known to be usable in a positive-type photoresist composition.

For example, the organic solvent may be at least one compound selected from the group consisting of ethylene glycol monomethyl ether, ethylene glycol monoethyl ether, ethylene glycol monobutyl ether, ethylene glycol monoacetate, diethylene glycol, diethylene glycol monoethyl ether, diethylene glycol methyl ethyl ether, propylene glycol, propylene glycol monoacetate, propylene glycol methyl ether acetate, toluene, xylene, methyl ethyl ketone, methyl isoamyl ketone, cyclohexanone, dioxane, methyl lactate, ethyl lactate, methyl pyruvate, ethyl pyruvate, methyl methoxypropionate, ethyl ethoxypropionate, N,N-dimethylformamide, N,N-dimethylacetamide, N-methyl-2-pyrrolidone, 3-ethoxyethyl propionate, 2-heptanone, gam ma-butyrolactone, ethyl 2-hydroxypropionate, ethyl 2-hydroxy-2-methylpropionate, ethyl ethoxyacetate, ethyl hydroxyacetate, methyl 2-hydroxy-3-methylbutanoate, methyl 3-methoxy-2-methyl propionate, ethyl 3-ethoxypropionate, ethyl 3-methoxy-2-methylpropionate, acetate, and butyl acetate.

The organic solvent may be included in an amount of 5 to 500 parts by weight, 5 to 450 parts by weight, or 5 to 400 parts by weight based on 100 parts by weight of the alkali developable resin. That is, in order to ensure the applicability of the composition, it is preferable that the organic solvent is included in an amount of 5 parts by weight or more based on 100 parts by weight of the alkali developing resin. However, when the organic solvent is included in an excess amount, the viscosity of the composition may be lowered, which may make it difficult to control the thickness of the photoresist. Therefore, it is preferable that the organic solvent is included in an amount of 500 parts by weight or less based on 100 parts by weight of the alkali developable resin.

Further, the photoacid generator may be included in an amount of 0.1 to 10 parts by weight, 0.5 to 10 parts by weight, or 1 to 5 parts by weight, based on 100 parts by weight of the alkali developable resin.

That is, the photoacid generator is preferably included in an amount of 0.1 parts by weight or more based on 100 parts by weight of the alkali developable resin, so that the photoacid generating effect can be fully manifested. However, when the photoacid generator is included in an excess amount, the photosensitivity of the composition may deviate from an appropriate level, and a scum may remain on an exposed part after development. Therefore, it is preferable that the photoacid generator is included in an amount of 10 parts by weight or less based on 100 parts by weight of the alkali developable resin.

In addition to the above-mentioned components, the chemically amplified positive-type photoresist composition for a thick film may include a surfactant, an acid diffusion controller, and the like.

The surfactant and acid diffusion controller can be used without limitation, as long as they are commonly used in the positive-type photoresist composition in the art.

The surfactant may be included in an amount of 0.01 to 1 parts by weight, 0.05 to 1 part by weight, or 0.05 to 0.5 parts by weight based on 100 parts by weight of the alkali developable resin. When the surfactant is included in an excess amount, wettability and flatness of the composition on the substrate may deviate from an appropriate level. Accordingly, the surfactant is preferably included in an amount of 1 part by weight or less based on 100 parts by weight of the alkali developable resin.

The acid diffusion controller may be included to improve the resist pattern shape, post-exposure stability, and the like. For example, it may be at least one selected from the group consisting of triethylamine, tripropyl amine, tribenzyl amine, trihydroxyethyl amine, and ethylene diamine.

Advantageous Effects

The compound including at least one functional group represented by Chemical Formula 1 may not only exhibit high solubility in a solvent of the photoresist composition, but may also exhibit chemical and thermal stability and high sensitivity. In particular, the compound can be added to a chemically amplified photoresist composition for a thick film as a non-ionic photoacid generator with a corrosion inhibiting effect.

DETAILED DESCRIPTION OF THE EMBODIMENTS

Hereinafter, preferred examples are provided for better understanding. However, these examples are for illustrative purposes only, and the invention is not intended to be limited by these examples.

SYNTHESIS EXAMPLE A

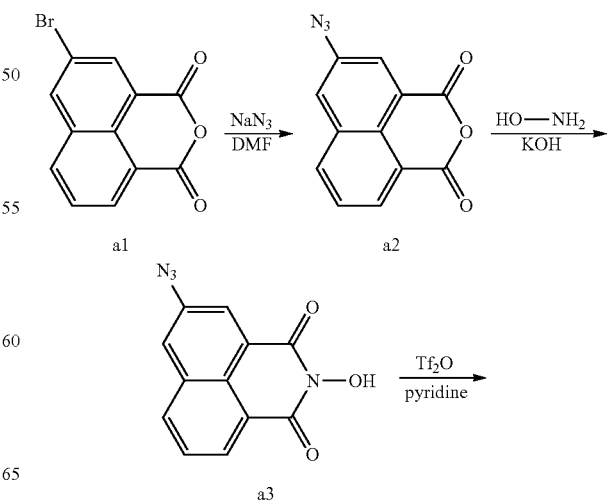

[Scheme A-1]

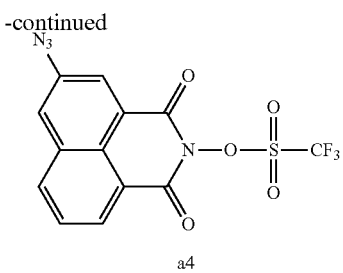

a4

Compound a1 (5-bromobenzo[de]isochromene-1,3-dione)

Compound a2 (5-azidobenzo[de]isochromene-1,3-dione)

Compound a3 (5-azido-2-hydroxy-1H-benzo[de]isoquinoline-1,3(2H)-dione)

Compound a4 (5-azido-1,3-dioxo-1H-benzo[de]isoquinolin-2(3H)-yl trifluoromethanesulfonate)

(1) Synthesis of Compound a2

Compound a1 (1.0 equiv.) was dissolved in dimethylformamide (DMF), and then $NaN_3$ (1.1 equiv.) was added thereto, followed by refluxing at 100° C. for 12 hours. Then, 20 g each of water and chloroform were added to the reaction solution, and the mixture was subjected to oil-water separation to obtain an organic layer, followed by washing once with 1 N hydrochloric acid and then five times with water. The solid phase obtained by concentrating the organic phase was dissolved in chloroform, and the filtrate obtained by filtration was recrystallized by adding methanol to the filtrate. The obtained crystals were taken by filtration and vacuum-dried at 45° C. to obtain 10 g of Compound a2 (95% yield).

$^1$H NMR (DMSO-$d_6$, Standard material TMS) δ(ppm): 8.78 (1H, d), 8.69-8.65 (3H, m), 8.01 (1H, t)

(2) Synthesis of Compound a3

Ethanol was added to a flask containing Compound a2 (1.0 equiv.), $NH_2OH$—HCl (hydroxylamine hydrochloride, 1.5 equiv.), and KOH (1.5 equiv.), and then refluxed for 1 hour to remove the solvent. Water and HCl (1 N) were added, and the resulting colorless solid was filtered off, followed by washing with diethyl ether to obtain 16 g of Compound a3 (73% yield).

$^1$H NMR (DMSO-$d_6$, Standard material TMS) δ(ppm): 8.42-8.35 (4H, m), 7.97 (1H, t)

(3) Synthesis of Compound a4

Compound a3 (1.0 equiv.) was dissolved in chloroform, and then pyridine (1.5 equiv.) was added thereto, followed by cooling to 0° C. $Tf_2O$ (trifluoromethanesulfonic anhydride, 1.3 equiv.) was added slowly thereto and stirred at room temperature for 3 hours. After the reaction was completed, water was added. Then, the separated organic layer was washed with a NaOH aqueous solution (0.2 N), HCl (1 N) and water, dried with magnesium sulfate, and filtered, followed by removing the solvent. 15 g of Compound a4 (53% yield) was obtained by column chromatography purification.

$^1$H NMR (DMSO-$d_6$, Standard material TMS) δ(ppm): 8.41-8.35 (4H, m), 7.87 (1H, t)

[Scheme A-2]

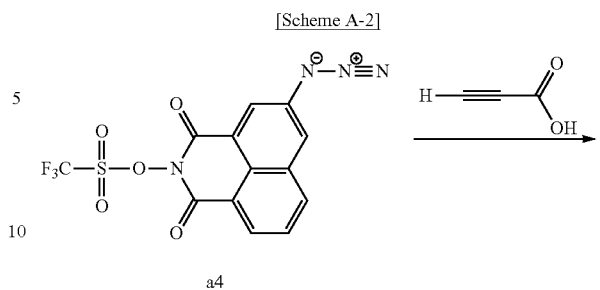

A

Compound A (1-(1,3-dioxo-2-(((trifluoromethyl)sulfonyl)oxy)-2,3-dihydro-1H-benzo[de]isoquinolin-5-yl)-1H-1,2,3-triazole-4-carboxylic acid) was obtained by a click reaction between the Compound a4 (5-azido-1,3-dioxo-1H-benzo[de]isoquinolin-2(3H)-yl trifluoromethanesulfonate) and propiolic acid.

Specifically, the Compound a4 and the propiolic acid were dissolved in chloroform in an amount of 1.0 equiv., respectively, and then the previously prepared catalyst solution (CuBr/PMDETA=1/1 mol/mol) (PMDETA:N,N,N',N'',N''-pentamethyldiethylenetriamine) was added thereto in an amount of 0.05 equiv. based on CuBr, followed by stirring for 12 hours. The reaction mixture was washed with water and HCl (1 N), and then the organic layer was concentrated and purified by column chromatography to obtain 24 g of Compound A (78% yield).

$^1$H NMR (DMSO-$d_6$, Standard material TMS) δ(ppm): 8.43-8.35 (4H, m), 8.08 (1H, s), 7.86 (1H, t)

SYNTHESIS EXAMPLE B

[Scheme B]

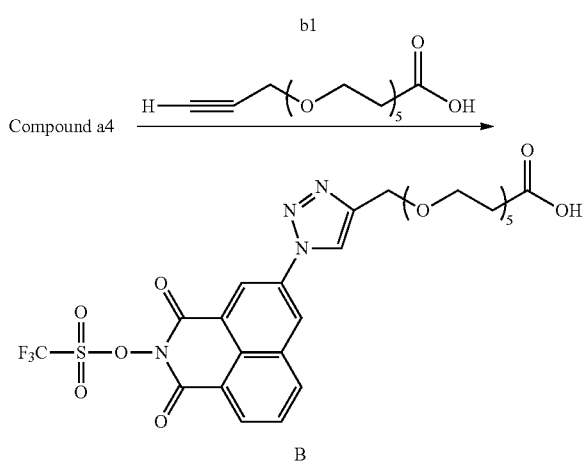

B

Compound B (1-(1-(1,3-dioxo-2-(((trifluoromethyl)sulfo-nyl)oxy)-2,3-dihydro-1H-benzo[de]isoquinolin-5-yl)-1H-1,2,3-triazol-4-yl)-2,5,8,11,14-pentaoxaheptadecan-17-oic acid) was obtained by a click reaction between the Compound a4 (5-azido-1,3-dioxo-1H-benzo[de]isoquinolin-2 (3H)-yl trifluoromethanesulfonate) and a Compound b1 (Alkyne-PEG5-acid).

Specifically, the Compound a4 and the Compound b1 were dissolved in chloroform in an amount of 1.0 equiv., respectively, and then the previously prepared catalyst solution (CuBr/PMDETA=1/1 mol/mol) (PMDETA:N,N,N',N",N"-pentamethyldiethylenetriamine) was added thereto in an amount of 0.05 equiv. based on CuBr, followed by stirring for 12 hours. The reaction mixture was washed with water and HCl (1 N), and then the organic layer was concentrated and purified by column chromatography to obtain 15 g of Compound B (56% yield).

$^1$H NMR (DMSO-$d_6$, Standard material TMS) δ(ppm): 8.41-8.36 (4H, m), 8.10 (1H, s), 7.88 (1H, t), 4.11 (2H,s), 3.60 (2H, t), 3.51 (16H, m), 2.40 (2H, t)

SYNTHESIS EXAMPLE C

[Scheme C]

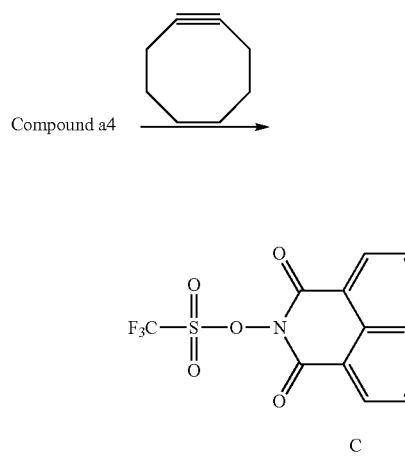

Compound C (5-(4,5,6,7,8,9-hexahydro-1H-cycloocta[d][1,2,3]triazol-1-yl)-1,3-dioxo-1H-benzo[de]isoquinolin-2 (3H)-yl trifluoromethanesulfonate) was obtained by a click reaction between the Compound a4 (5-azido-1,3-dioxo-1H-benzo[de]isoquinolin-2(3H)-yl trifluoromethanesulfonate) and cyclooctyne.

Specifically, the Compound a4 and the cyclooctyne were dissolved in chloroform in an amount of 1.0 equiv., respectively, and then the previously prepared catalyst solution (CuBr/PMDETA=1/1 mol/mol) (PMDETA:N,N,N',N",N"-pentamethyldiethylenetriamine) was added thereto in an amount of 0.05 equiv. based on CuBr, followed by stirring for 12 hours. The reaction mixture was washed with water and HCl (1 N), and then the organic layer was concentrated and purified by column chromatography to obtain 21 g of Compound C (60% yield).

$^1$H NMR (DMSO-$d_6$, Standard material TMS) δ(ppm): 8.41-8.34 (4H, m), 7.88 (1H, t), 2.65 (4H,t), 1.74 (4H, m), 1.32 (4H, t)

SYNTHESIS EXAMPLE D

[Scheme D-1]

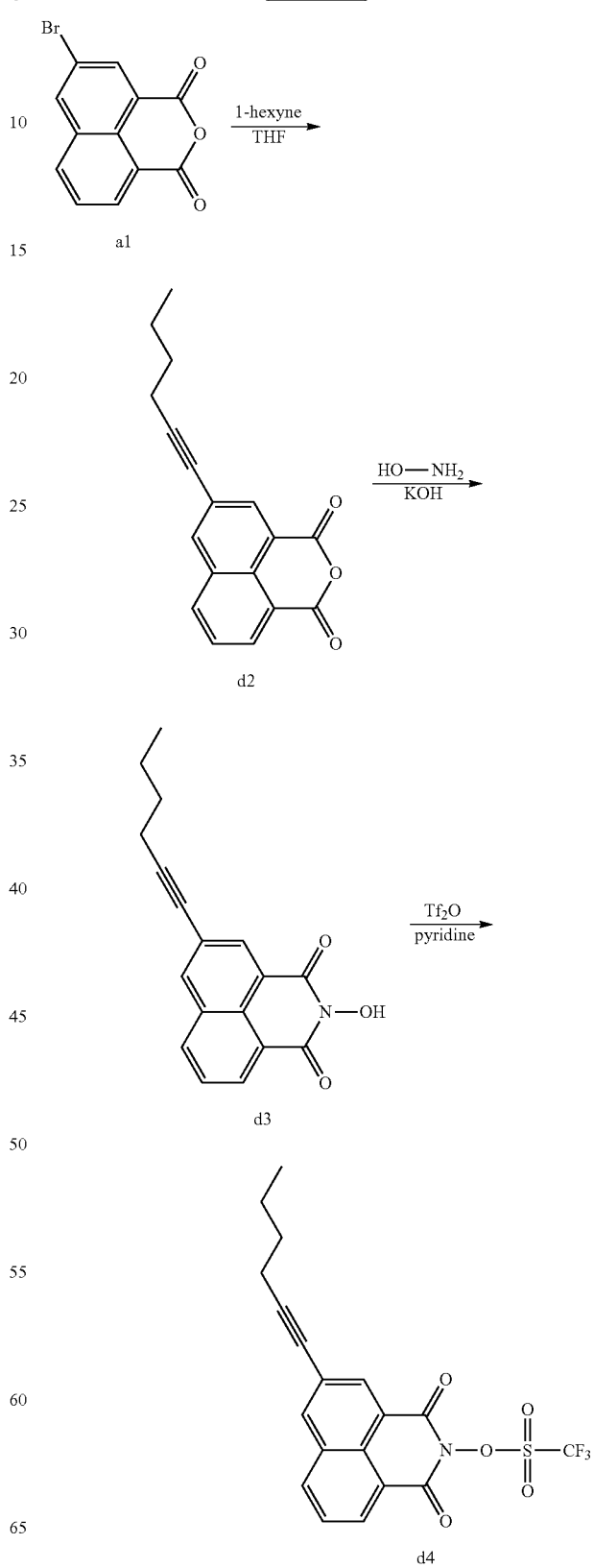

Compound a1 (5-bromobenzo[de]isochromene-1,3-dione)

Compound d2 (5-(hex-1-yn-1-yl)benzo[de]isochromene-1,3-dione)

Compound d3 (5-(hex-1-yn-1-yl)-2-hydroxy-1H-benzo[de]isoquinoline-1,3(2H)-dione)

Compound d4 (5-(hex-1-yn-1-yl)-1,3-dioxo-1H-benzo[de]isoquinolin-2(3H)-yl trifluoromethanesulfonate)

(1) Synthesis of Compound d2

Under a nitrogen atmosphere, Compound a1 (1.0 equiv.) was dissolved in tetrahydrofuran (THF), and then triphenylphosphine (PPh3) (0.08 equiv.) and triethylamine (TEA) (2.0 equiv.) were added thereto, followed by mixing for 1 hour. Then, CuI (0.03 equiv.) and Pd(PPh3)$_2$Cl$_2$ (0.01 equiv.) were added to the reaction solution, and 1-hexyne (1.0 equiv.) was slowly added dropwise over 3 hours.

Thereafter, the mixture was reacted for 15 hours while refluxing, and the temperature was lowered to room temperature. Then, 20 g of water was added thereto and the mixture was filtered to obtain a solid material. The solid was subjected to oil-water separation to obtain an organic layer. Then, the solid phase obtained by concentrating the organic layer was dissolved in acetonitrile (CAN), and recrystallized. The obtained crystals were taken by filtration and vacuum-dried at 45° C. to obtain 25 g of Compound d2 (70% yield).

$^1$H NMR (DMSO-d$_6$, Standard material TMS) δ(ppm): 8.75-8.71 (2H, m), 8.57 (1H, s), 8.40 (1H, s), 8.03 (1H, t), 2.46 (2H, t), 1.44 (2H, m), 1.32 (2H, m), 0.89 (3H, t)

(2) Synthesis of Compound d3

Ethanol was added to a flask containing Compound d2 (1.0 equiv.), NH$_2$OH—HCl (hydroxylamine hydrochloride, 1.5 equiv.), and KOH (1.5 equiv.), and then refluxed for 1 hour to remove the solvent. Water and HCl (1 N) were added, and the resulting colorless solid was filtered off, followed by washing with diethyl ether to obtain 21 g of Compound d3 (52% yield).

$^1$H NMR (DMSO-d$_6$, Standard material TMS) δ(ppm): 8.42-8.38 (2H, m), 8.28 (1H, s), 8.11 (1H, s), 7.89 (1H, t), 2.46 (2H, t), 1.44 (2H, m), 1.30 (2H, m), 0.89 (3H, t)

(3) Synthesis of Compound d4

Compound d3 (1.0 equiv.) was dissolved in chloroform, and then pyridine (1.5 equiv.) was added thereto, followed by cooling to 0° C. Tf$_2$O (trifluoromethanesulfonic anhydride, 1.3 equiv.) was slowly added thereto and stirred at room temperature for 3 hours. After the reaction was completed, water was added. Then, the separated organic layer was washed with a NaOH aqueous solution (0.2 N), HCl (1 N), and water, dried with magnesium sulfate, and filtered, followed by removing the solvent. 17 g of Compound d4 (65% yield) was obtained by column chromatography purification.

$^1$H NMR (DMSO-d$_6$, Standard material TMS) δ(ppm): 8.44-8.40 (2H, m), 8.30 (1H, s), 8.11 (1H, s), 7.90 (1H, t), 2.46 (2H, t), 1.44 (2H, m), 1.30 (2H, m), 0.89 (3H, t)

[Scheme D-2]

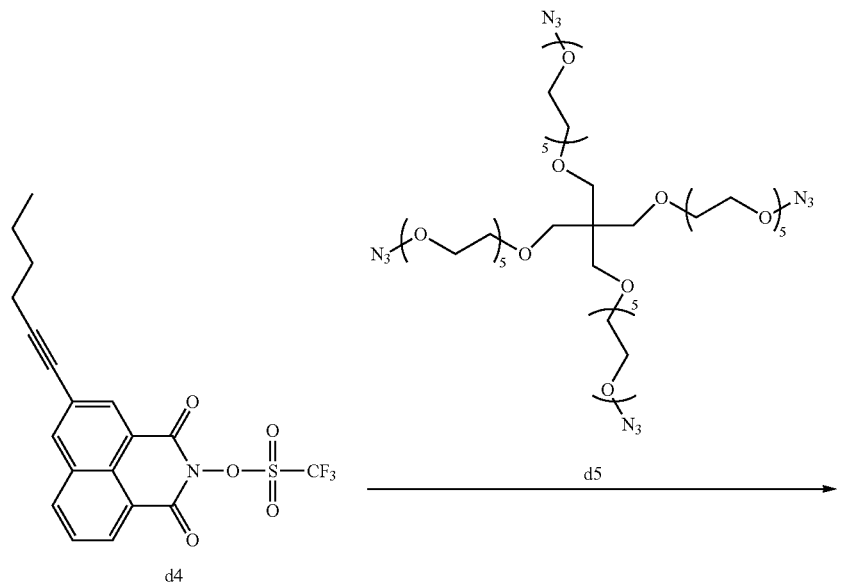

-continued

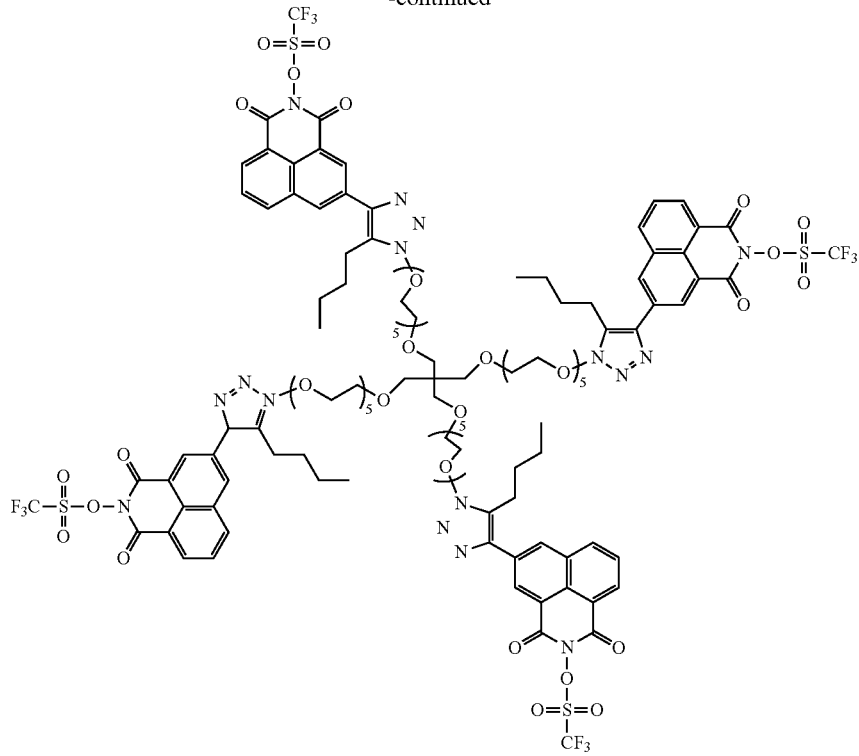

D

Compound D was obtained by a click reaction between the Compound d4 (5-(hex-1-yn-1-yl)-1,3-dioxo-1H-benzo[de]isoquinolin-2(3H)-yl trifluoromethanesulfonate) and Compound d5 (4-Arm PEG-Azide: a multiarm PEG derivative with azido (N3) groups at each terminal of the four arms connected to one pentaerythritol core).

Specifically, the Compounds d4 and d5 (4-Arm PEG-Azide) were dissolved in chloroform in an amount of 1.0 equiv., respectively, and then the previously prepared catalyst solution (CuBr/PMDETA=1/1 mol/mol) (PMDETA:N,N,N',N'',N''-pentamethyldiethylenetriamine) was added thereto in an amount of 0.05 equiv. based on CuBr, followed by stirring for 12 hours. The reaction mixture was washed with water and HCl (1 N), and then the organic layer was concentrated and purified by recrystallization to obtain 42 g of Compound D (83% yield).

$^1$H NMR (DMSO-$d_6$, Standard material TMS) δ(ppm): 8.44-8.40 (8H, m), 8.30 (4H, s), 8.11 (4H, s), 7.90 (4H, t), 3.79 (8H, s), 3.70 (16H, t), 3.54-3.52 (72H, m), 2.44 (8H, t), 1.62 (8H, m), 1.33 (8H, m), 1.06 (12H, t)

EXAMPLES 1 TO 8

The components shown in Table 1 below were mixed to prepare chemically amplified positive-type photoresist compositions for a thick film of Examples 1 to 8, respectively.

Specifically, the photoresist composition was prepared by mixing 100 g of the alkali developable resin (R1-R3), 5 g of the photoacid generator (A1-A4), and 10 g of the organic solvent (PGMEA).

In the following Table 1, the components applied to the above examples are as follows.

[R1] m,p-Cresol novolac resin (Mw 12,000 g/mol, ADR 500 Å/s)

[R2] Acetal protected polyhydroxystyrene (PHS) resin (Mw 15,300 g/mol, Substitution rate 25%)

[R3] Acrylic resin (Mw 65,000 g/mol)

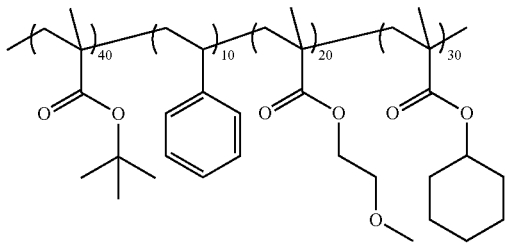

[A1] The photoacid generator (Compound A according to Synthesis Example A)

[A2] The photoacid generator (Compound B according to Synthesis Example B)

[A3] The photoacid generator (Compound C according to Synthesis Example C)

[A4] The photoacid generator (Compound D according to Synthesis Example D)

COMPARATIVE EXAMPLES 1 TO 3

The components shown in Table 1 below were mixed to prepare chemically amplified positive-type photoresist compositions for a thick film of Comparative Examples 1 to 3, respectively.

Specifically, the photoresist composition was prepared by mixing 100 g of the alkali developable resin (R1-R3), 1 g of the photoacid generator (NIT), 1 g of the corrosion inhibitor (BTA), and 10 g of the organic solvent (PGMEA).

In the following Table 1, NIT and BTA of the above comparative examples are as follows.

[NIT] 1,3-Dioxo-1H-benzo[de]isoquinolin-2(3H)-yl trifluoromethanesulfonate

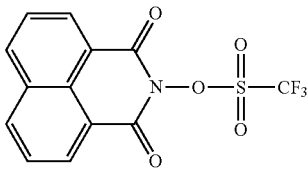 [SMILES: O=C1c2cccc3cccc(c23)C(=O)N1OS(=O)(=O)C(F)(F)F]

[BTA] Benzotriazole

TABLE 1

|  | R1 | R2 | R3 | A1 | A2 | A3 | A4 | NIT | BTA |
|---|---|---|---|---|---|---|---|---|---|
| Example 1 | 40 | — | 60 | 5 | — | — | — | — | — |
| Example 2 | 40 | — | 60 | — | 5 | — | — | — | — |
| Example 3 | 40 | — | 60 | — | — | 5 | — | — | — |
| Example 4 | 40 | — | 60 | — | — | — | 5 | — | — |
| Example 5 | — | 30 | 70 | — | 5 | — | — | — | — |
| Example 6 | — | 30 | 70 | — | — | — | 5 | — | — |
| Example 7 | — | — | 100 | — | 5 | — | — | — | — |
| Example 8 | — | — | 100 | — | — | — | 5 | — | — |
| Comp. Ex. 1 | 40 | — | 60 | — | — | — | — | 1 | 1 |
| Comp. Ex. 2 | — | 30 | 70 | — | — | — | — | 1 | 1 |
| Comp. Ex. 3 | — | — | 100 | — | — | — | — | 1 | 1 |

The content of the components listed in the Table 1 is based on the solid content. The sum of the alkali developable resin is 100 parts by weight, and the photoacid generator and the corrosion inhibitor are based on 100 parts by weight of the alkali developable resin.

EXPERIMENTAL EXAMPLES

Using the respective photoresist compositions according to the examples and comparative examples, semiconductor devices were patterned in the following manner.

The photoresist composition was spin-coated on a 4-inch Si wafer coated with copper (Cu) to a thickness of about 2000 Å, and dried at 120° C. for 4 minutes to form a photoresist layer of about a 50 μm thickness. The wafer was exposed using an i-line stepper (equipped with a photomask having hole patterns of about 10, 20, 30, 40, and 50 μm size). The exposed wafer was dried at 100° C. for 3 minutes, and then developed for 300 seconds using a developing solution (about 2.38 wt % tetramethylammonium hydroxide aqueous solution).

After the patterning, physical properties of the photoresist composition were evaluated in the following manner.

(1) Sensitivity (Exposure Dose, mJ/cm$^2$)

The photoresist compositions prepared in Examples 1 to 8 and Comparative Examples 1 to 3 were spin-coated on a glass substrate and dried on a hot plate at 120° C. for 2 minutes. Then, they were exposed using a step mask, further dried on the hot plate at 100° C. for 2 minutes, and then developed in an aqueous solution of tetramethylammonium hydroxide (TMAH). The exposure dose of the step mask pattern and the photoresist (PR) pattern with the same CD size was evaluated as sensitivity.

(2) Occurrence of Footing at Lower Part of Pattern

The photoresist compositions prepared in Examples 1 to 8 and Comparative Examples 1 to 3 were spin-coated on a glass substrate and dried on a hot plate at 120° C. for 2 minutes. Then, they were exposed using a step mask, further dried on the hot plate at 100° C. for 2 minutes, and then developed in an aqueous solution of tetramethylammonium hydroxide (TMAH). A reduced value of the hole diameter from the top to the bottom of the thick film resist pattern was evaluated as a footing length. The footing property of the PR was evaluated based on the following criteria.

⊚: A footing length of more than 0 nm and 200 nm or less
○: A footing length of more than 200 nm and 500 nm or less
Δ: A footing length of more than 500 nm and 1 μm or less
×: A footing length of more than 1 μm (3) Developability (Presence or Absence of Residue)

A thick film resist pattern was prepared in the same manner as the occurrence of footing at lower part of pattern, and presence or absence of residue in the developing part was observed to be an index of developability. The developability was evaluated based on the following criteria.

⊚: No residue formed
Δ: Some residue formed around the pattern
×: Residue formed in the whole developing part (4) Resistance to Plating Solution The photoresist compositions prepared in Examples 1 to 8 and Comparative Examples 1 to 3 were applied on a substrate using a spin coater, and then subjected to a process such as prebake and postbake to form a resist film. The resist film was immersed in a Cu plating solution at room temperature for 24 hours to examine whether there was a change in thickness of the resist film. The rate of change in thickness was evaluated based on the following criteria.

⊚: A rate of change in thickness of within 1%
○: A rate of change in thickness of more than 1% and 3% or less
Δ: A rate of change in thickness of more than 3% and 10% or less
×: A rate of change in thickness of more than 10%

(5) Heat Resistance

The photoresist compositions prepared in Examples 1 to 8 and Comparative Examples 1 to 3 were spin-coated on a glass substrate and dried on a hot plate at 120° C. for 2 minutes. Then, they were exposed using a step mask, and further dried on the hot plate at 100° C. for 2 minutes. Thereafter, the coated wafer was tilted at 45° for 20 seconds and developed in an aqueous solution of tetramethylammonium hydroxide (TMAH). The heat resistance was evaluated based on the following criteria by measuring how much the prepared thick film resist pattern tilted sideways (perpendicularity of the pattern slope).

⊚: No tilt
○: More than 0° and 5° or less
Δ: More than 5° and 10° or less
×: More than 10°

TABLE 2

|  | Sensitivity (mJ/cm$^2$) | Footing | Developability | Resistance to Plating solution | Heat resistance |
|---|---|---|---|---|---|
| Example 1 | 350 | ○ | ⊚ | ○ | ⊚ |
| Example 2 | 310 | ○ | ⊚ | ○ | ⊚ |
| Example 3 | 340 | ○ | ⊚ | ○ | ⊚ |
| Example 4 | 280 | ○ | ⊚ | ○ | ⊚ |
| Example 5 | 210 | ⊚ | ⊚ | ⊚ | ⊚ |
| Example 6 | 180 | ⊚ | ⊚ | ⊚ | ⊚ |
| Example 7 | 250 | ○ | ⊚ | ⊚ | ⊚ |
| Example 8 | 210 | ○ | ⊚ | ⊚ | ⊚ |
| Comp. Ex. 1 | 870 | X | ⊚ | X | ○ |

TABLE 2-continued

| | Sensitivity (mJ/cm$^2$) | Footing | Developability | Resistance to Plating solution | Heat resistance |
|---|---|---|---|---|---|
| Comp. Ex. 2 | 790 | X | Δ | Δ | ○ |
| Comp. Ex. 3 | 990 | X | X | Δ | ○ |

Referring to Table 2 above, the photoresist compositions according to the examples showed excellent sensitivity and developability at a low exposure dose, and were confirmed to exhibit excellent resistance to the plating solution even without a separate corrosion inhibitor (NIT).

The invention claimed is:

1. A non-ionic photoacid generator comprising at least one functional group represented by the following Chemical Formula 1:

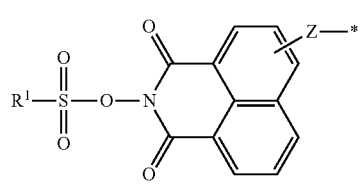

[Chemical Formula 1]

wherein, in Chemical Formula 1,

R$^1$ is a C1 to C10 aliphatic hydrocarbon group substituted or unsubstituted with at least one of a halogen atom, an alkylthio group, and an alicyclic hydrocarbon group; a C1 to C10 perfluoroalkyl group; a C6 to C20 aryl group substituted or unsubstituted with at least one of a halogen atom, an alkylthio group, an alkyl group, and an acyl group; or a C7 to C20 arylalkyl group substituted or unsubstituted with a halogen atom and an alkylthio group, and Z is a group represented by the following Chemical Formula 2b:

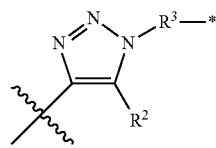

[Chemical Formula 2b]

wherein, in Chemical Formula 2b,

R$^2$ is hydrogen, a C3 to C10 alkyl group, or a C1 to C10 hydroxyalkyl group,

R$^3$ is a chemical bond, a C1 to C10 alkylene group, or a group represented by the following Chemical Formula 3, and when R$^2$ is a C3 to C10 alkyl group and R$^3$ is a C1 to C10 alkylene group, they are connected to each other to form a C4 to C20 aliphatic ring,

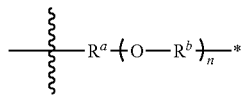

[Chemical Formula 3]

wherein, in Chemical Formula 3,

R$^a$ is a chemical bond or a C1 to C10 alkylene group,

R$^b$ is a C1 to C10 alkylene group, n is an integer of 1 to 10, and when n is 2 or more, each R$^b$, which is repeated two or more times, is the same or different from each other.

2. The non-ionic photoacid generator of claim 1, wherein the non-ionic photoacid generator is represented by the following Chemical Formula 5a or 5b:

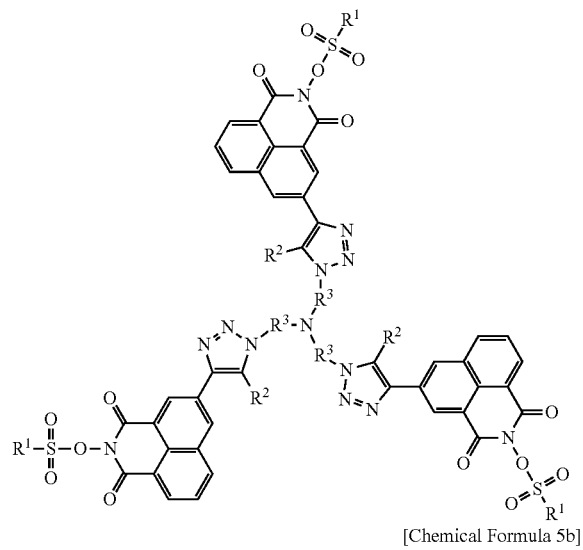

[Chemical Formula 5a]

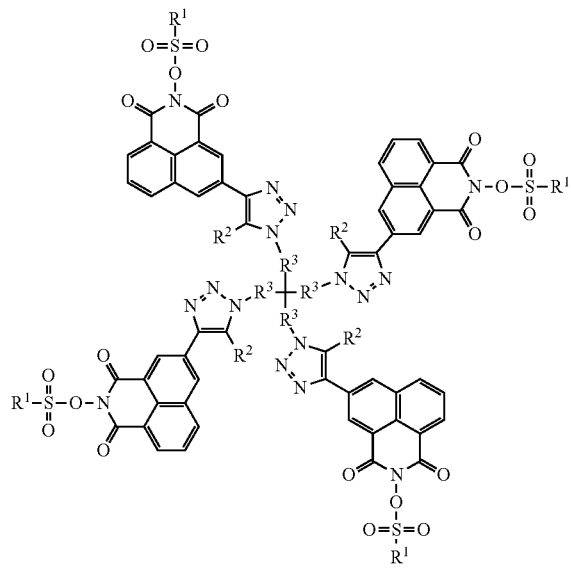

[Chemical Formula 5b]

wherein, in Chemical Formulae 5a and 5b,

R$^1$, R$^2$, and R$^3$ are as defined above in Chemical Formulae 1, 2b, and 3.

3. A chemically amplified positive-type photoresist composition for a thick film comprising the non-ionic photoacid generator of claim 2.

4. A chemically amplified positive-type photoresist composition for a thick film comprising the non-ionic photoacid generator of claim 1.

5. The chemically amplified positive-type photoresist composition for a thick film of claim 4, wherein the composition does not comprise a separate corrosion inhibitor.

6. The chemically amplified positive-type photoresist composition for a thick film of claim 4, wherein the composition further comprises an alkali developable polymer resin, a photoinitiator and an organic solvent.

7. The non-ionic photoacid generator of claim 1, comprising one, two, three or four functional groups represented by Chemical Formula 1 as defined in claim 1.

8. The non-ionic photoacid generator of claim 1, wherein $R^1$ is methyl, ethyl, propyl, isopropyl, butyl, sec-butyl, tert-butyl, isobutyl, amyl, isoamyl, tert-amyl, hexyl, 2-hexyl, 3-hexyl, heptyl, 2-heptyl, 3-heptyl, isoheptyl, tert-heptyl, octyl, isooctyl, tert-octyl, 2-ethylhexyl, nonyl, isononyl, decyl, dodecyl, tridecyl, tetradecyl, pentadecyl, hexadecyl, heptadecyl, octadecyl, trifluoromethyl, pentafluoroethyl, heptafluoropropyl, nonafluorobutyl, tridecylfluorohexyl, heptafluorooctyl, 2,2,2-trifluoroethyl, 1,1-difluoroethyl, 1,1-difluoropropyl, 1,1,2,2-tetrafluoropropyl, 3,3,3-trifluoropropyl, 2,2,3,3,3-pentafluoropropyl, 1,1,2,2-tetrafluorotetradecyl, phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, 2,5-di-tert-butylphenyl, 2,6-di-tert-butylphenyl, 2,4-di-tert-pentylphenyl, 2,5-di-tert-amylphenyl, 2,5-di-tert-octylphenyl, cyclohexylphenyl, biphenyl, 2,4,5-trimethylphenyl, 2,4,6-trimethylphenyl, 2,4,6-triisopropylphenyl, pentafluorophenyl, chlorophenyl, dichlorophenyl, trichlorophenyl, 2,4-bis(trifluoromethyl)phenyl, bromoethylphenyl, 4-methylthiophenyl, 4-butylthiophenyl, 4-octylthiophenyl, 4-dodecylthiophenyl, 1,2,5,6-tetrafluoro-4-methylthiophenyl, 1,2,5,6-tetrafluoro-4-butylthiophenyl, 1,2,5,6-tetrafluoro-4-dodecylthiophenyl, benzyl, phenethyl, 2-phenylpropan-2-yl, diphenylmethyl, triphenylmethyl, styryl, cinnamyl, pentafluorophenylmethyl, phenyldifluoromethyl, 2-phenyl-tetrafluoroethyl, 2-(pentafluorophenyl)ethyl, p-methylthiobenzyl, 2,3,5,6-tetrafluoro-4-methylthiophenylethyl, acetylphenyl, acetylnaphthyl, benzoylphenyl, 1-anthraquinolyl, or 2-anthraquinolyl group.

9. A non-ionic photoacid generator comprising at least one functional group represented by the following Chemical Formula 4a or 4b:

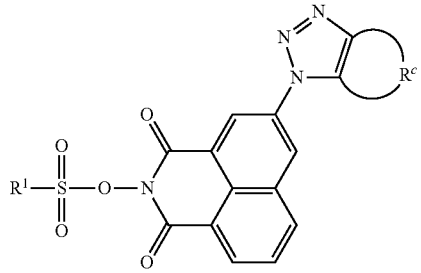
[Chemical Formula 4a]

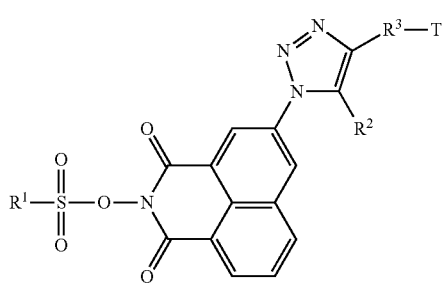
[Chemical Formula 4b]

wherein, in Chemical Formulae 4a and 4b,
$R^1$ is a C1 to C10 aliphatic hydrocarbon group substituted or unsubstituted with at least one of a halogen atom, an alkylthio group, and an alicyclic hydrocarbon group; a C1 to C10 perfluoroalkyl group; a C6 to C20 aryl group substituted or unsubstituted with at least one of a halogen atom, an alkylthio group, an alkyl group, and an acyl group; or a C7 to C20 arylalkyl group substituted or unsubstituted with a halogen atom and an alkylthio group,
$R^2$ is hydrogen, a C3 to C10 alkyl group, or a C1 to C10 hydroxyalkyl group,
$R^3$ is a chemical bond, a C1 to C10 alkylene group, or a group represented by the following Chemical Formula 3, and
when $R^2$ is a C3 to C10 alkyl group and $R^3$ is a C1 to C10 alkylene group, they are connected to each other to form a C4 to C20 aliphatic ring,

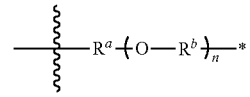
[Chemical Formula 3]

wherein, in Chemical Formula 3,
$R^a$ is a chemical bond or a C1 to C10 alkylene group,
$R^b$ is a C1 to C10 alkylene group,
n is an integer of 1 to 10, and
when n is 2 or more, each $R^b$, which is repeated two or more times, is the same or different from each other,
T is —H, —(C=O)OH, —O—(C=O)OH, —(C=O)NH$_2$, —NH—(C=O)H, —OCH$_3$, —SH, —NH$_2$, —NO$_2$, —CF$_3$, or —SF$_3$, and
$R^c$ is a C4 to C20 aliphatic ring.

10. A chemically amplified positive-type photoresist composition for a thick film comprising the non-ionic photoacid generator of claim 9.

11. The chemically amplified positive-type photoresist composition for a thick film of claim 10, wherein the composition does not comprise a separate corrosion inhibitor.

12. The chemically amplified positive-type photoresist composition for a thick film of claim 10, wherein the composition further comprises an alkali developable polymer resin, a photoinitiator and an organic solvent.

13. The non-ionic photoacid generator of claim 9, comprising one, two, three or four functional groups represented by Chemical Formulae 4a or 4b as defined in claim 9.

14. The non-ionic photoacid generator of claim 9, wherein $R^1$ is methyl, ethyl, propyl, isopropyl, butyl, sec-butyl, tert-butyl, isobutyl, amyl, isoamyl, tert-amyl, hexyl, 2-hexyl, 3-hexyl, heptyl, 2-heptyl, 3-heptyl, isoheptyl, tert-heptyl, octyl, isooctyl, tert-octyl, 2-ethylhexyl, nonyl, isononyl, decyl, dodecyl, tridecyl, tetradecyl, pentadecyl, hexadecyl, heptadecyl, octadecyl, trifluoromethyl, pentafluoroethyl, heptafluoropropyl, nonafluorobutyl, tridecylfluorohexyl, heptafluorooctyl, 2,2,2-trifluoroethyl, 1,1-difluoroethyl, 1,1-difluoropropyl, 1,1,2,2-tetrafluoropropyl, 3,3,3-trifluoropropyl, 2,2,3,3,3-pentafluoropropyl, 1,1,2,2-tetrafluorotetradecyl, phenyl, naphthyl, 2-methylphenyl, 3-methylphenyl, 4-methylphenyl, 4-vinylphenyl, 3-isopropylphenyl, 4-isopropylphenyl, 4-butylphenyl, 4-isobutylphenyl, 4-tert-butylphenyl, 4-hexylphenyl, 4-cyclohexylphenyl, 4-octylphenyl, 4-(2-ethylhexyl)phenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4-di-tert-butylphenyl, 2,5-di-tert-butylphenyl, 2,6-di-tert-butylphenyl, 2,4-di-tert-pentylphenyl, 2,5-di-tert-amylphenyl, 2,5-di-tert-octylphenyl, cyclohexylphenyl, biphenyl, 2,4,5-trimethylphenyl, 2,4,6-trimethylphenyl, 2,4,6-triisopropylphenyl, pentafluorophenyl, chlorophenyl, dichlorophenyl, trichlorophenyl, 2,4-bis(trifluoromethyl)phenyl, bromoethylphenyl, 4-methylthiophenyl, 4-butylthiophenyl, 4-octylthiophenyl, 4-dodecylthiophenyl, 1,2,5,6-tetrafluoro-4-methylthiophenyl, 1,2,5,6-tetrafluoro-4-butylthiophenyl, 1,2,5,6-tetrafluoro-4-dodecylthiophenyl, benzyl, phenethyl, 2-phenylpropan-2-yl, diphenylmethyl, triphenylmethyl, styryl, cinnamyl, pentafluorophenylmethyl, phenyldifluoromethyl, 2-phenyl-tetrafluoroethyl, 2-(pentafluorophenyl)ethyl, p-methylthiobenzyl, 2,3,5,6-tetrafluoro-4-methylthiophenylethyl, acetylphenyl, acetylnaphthyl, benzoylphenyl, 1-anthraquinolyl, or 2-anthraquinolyl group.

\* \* \* \* \*